United States Patent
Kapral

(12) 
(10) Patent No.: US 6,190,419 B1
(45) Date of Patent: Feb. 20, 2001

(54) METHOD OF WASHING GARMENTS UTILIZING FLUORIC ACID

(76) Inventor: Ales M. Kapral, 12800 Reddington R., Tucson, AZ (US) 85749

( * ) Notice: Under 35 U.S.C. 154(b), the term of this patent shall be extended for 0 days.

(21) Appl. No.: 09/307,514

(22) Filed: May 7, 1999

Related U.S. Application Data

(63) Continuation-in-part of application No. 08/888,948, filed on Jul. 7, 1997, now Pat. No. 5,980,873.

(51) Int. Cl.$^7$ .................................................. C11D 7/12
(52) U.S. Cl. ............................................ 8/137; 510/529
(58) Field of Search ................................ 8/137; 510/529

(56) References Cited

U.S. PATENT DOCUMENTS

| | | | |
|---|---|---|---|
| 3,909,476 | * | 9/1975 | Mandell, Jr. .................... 260/29.6 H |
| 4,057,503 | * | 11/1977 | Graver et al. ......................... 252/8.7 |
| 4,115,281 | * | 9/1978 | Ciko et al. ............................ 252/8.8 |
| 4,120,650 | * | 10/1978 | Kappler et al. .......................... 8/109 |
| 4,154,578 | * | 5/1979 | Bane ........................................ 8/137 |
| 4,497,850 | * | 2/1985 | Umezono et al. .................... 427/127 |
| 5,112,358 | * | 5/1992 | Deal, III ................................. 8/137 |
| 5,221,423 | * | 6/1993 | Sugino et al. ........................ 156/643 |
| 5,718,729 | * | 2/1998 | Harris ...................................... 8/137 |
| 5,980,873 | * | 11/1999 | Mandell, Jr. .................... 260/29.6 H |

FOREIGN PATENT DOCUMENTS 0 494 025 A2 * 7/1992 (EP) ............................... C11D/3/04

* cited by examiner

Primary Examiner—Margaret Einsmann
Assistant Examiner—Christine Ingersoll
(74) Attorney, Agent, or Firm—Mark E. Ogram

(57) ABSTRACT

A composition which incorporates a metallic salt of fluoric acid is used as an additive for washing. When used in the "wash cycle", the metallic salt of fluoric acid increases the cleaning affect of the detergent and also increases the "fluff" of the clothes. Application of the fluoric acid is through a variety of mechanisms including: direct deposit of a quantity of liquid dilute containing the fluoric acid; application of an absorbent material containing the fluoric acid within the wash; and, inclusion of the fluoric acid within the detergent.

12 Claims, 3 Drawing Sheets

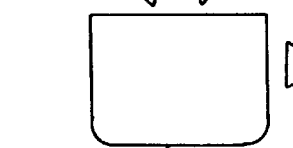
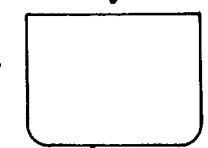
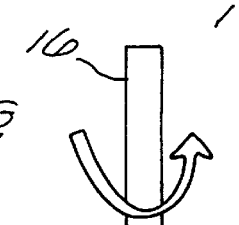
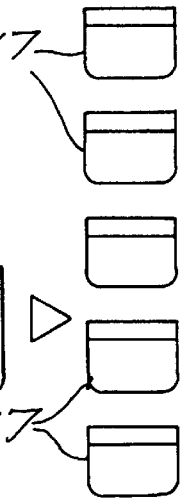
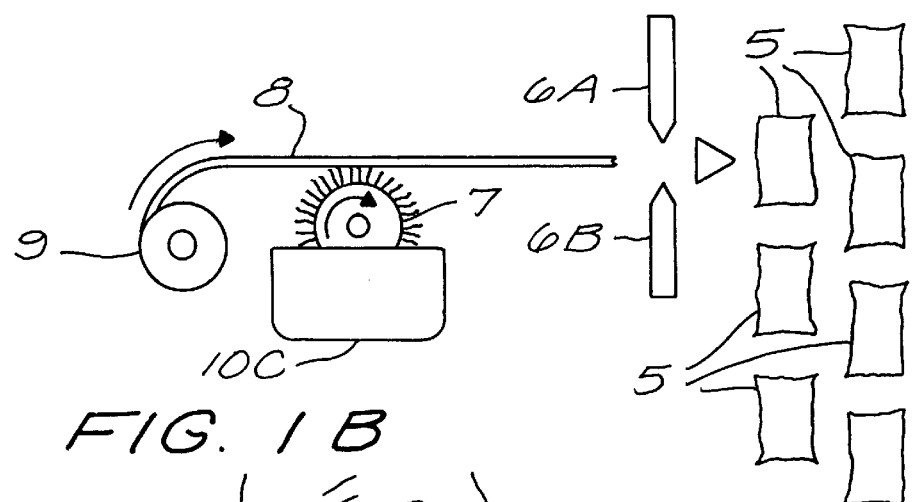
FIG. 1A
FIG. 1B
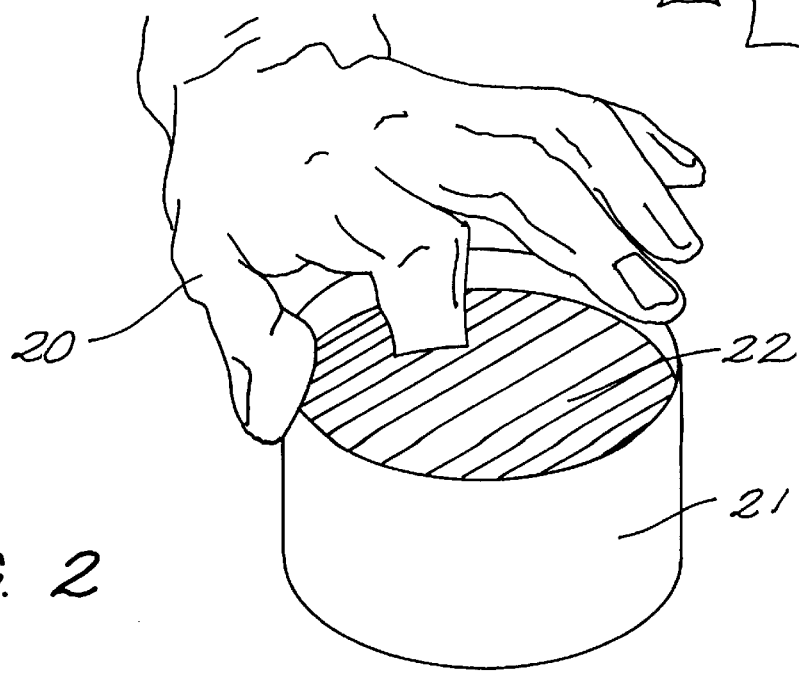
FIG. 2

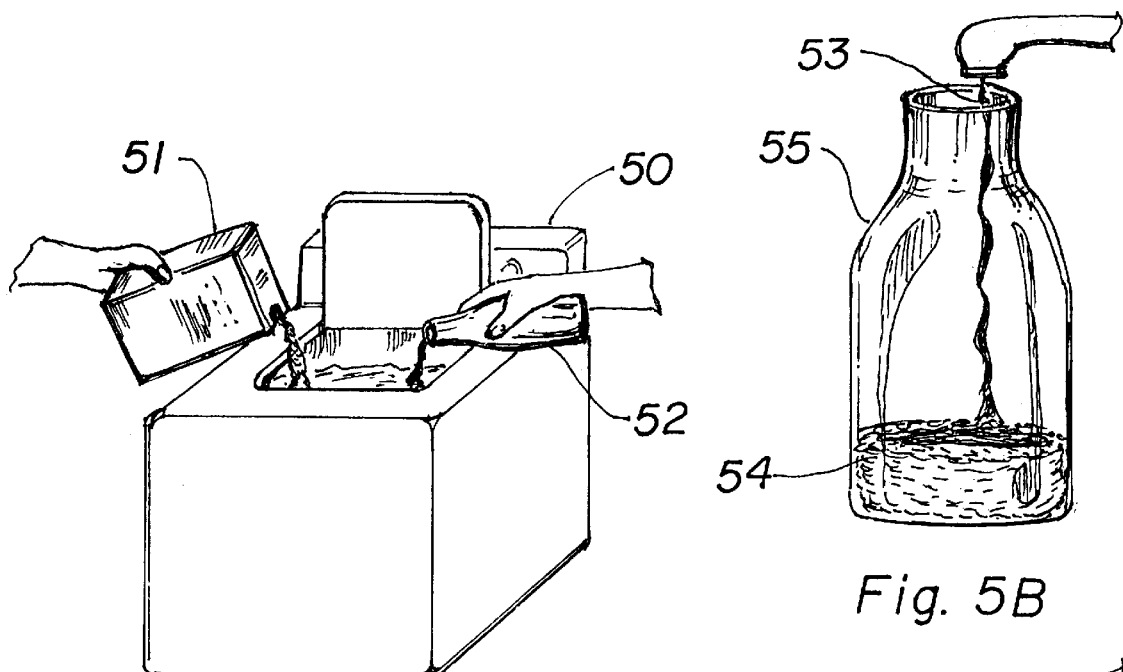
Fig. 5A
Fig. 5B
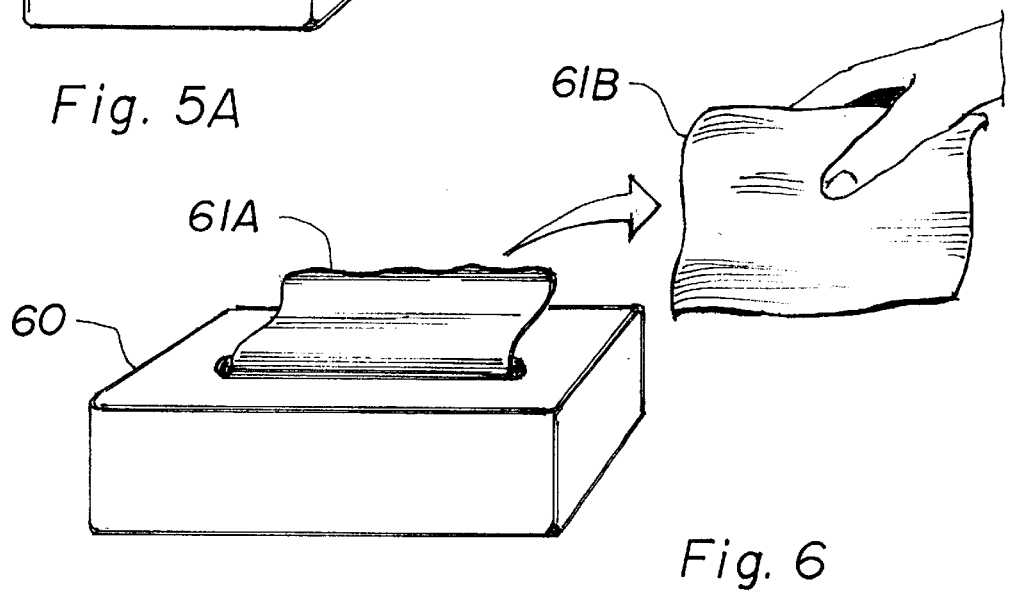
Fig. 6
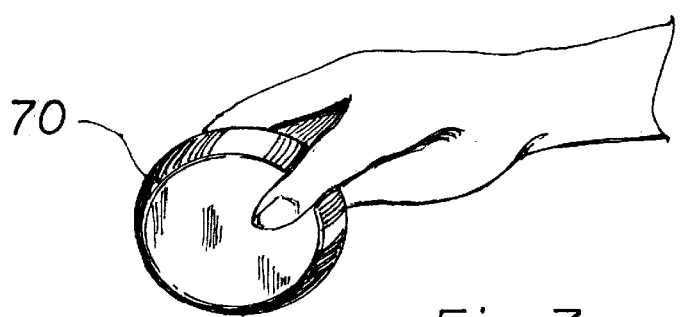
Fig. 7

METHOD OF WASHING GARMENTS UTILIZING FLUORIC ACID

This is a continuation-in-part of U.S. patent application Ser. No. 08/888,948, filed on Jul. 7, 1997 and entitled, "Additive for Cosmetics and Other Topically Applied Materials", now U.S. Pat. No. 5,980,873.

BACKGROUND OF THE INVENTION

This invention relates generally to washing and more particularly to the washing of clothes and dishes.

The present invention relates to a wide range of applications. In one application, the invention is useful in the field of cosmetics.

A wide assortment of creams, cosmetics, soaps, and medicines are applied to the topical layer of the skin with the intended affect of addressing a condition of the skin. Some examples of treatments include conditions of dry skin and acne.

The effectiveness of the treatment is directly related to the permeability of the material to the user's skin. If the active ingredient is unable to reach beneath the skin, the affect of the active ingredient is, at best, limited.

One such active ingredient is keratin which is used for the treatment of a variety of skin conditions and is also incorporated into soaps and creams to improve the user's skin. Unfortunately, keratin does not readily permeate the skin layer, hence, the vast majority of the keratin applied is simply washed or worn off without having the desired affect.

Another application for the invention is within the field of cleaning of items such as clothes, surgical scrubs, and dishes.

Cleaning through laundry, whether it is done in the home or in a commercial setting, constitutes a continuing chore. A wide assortment of detergents, pre-washes, and stain removers have been developed to assist in this chore.

Unfortunately, these chemicals are difficult to use and often do not remove many of the stains encountered. Further, these chemicals, after repetitive uses, tend to "flatten" or conceal the garment's color.

It is clear that there is a need for an easy to use and effective additive to assist in the cleaning of clothes, garments, and other items.

SUMMARY OF THE INVENTION

The invention provides a keratin composition which incorporates a metallic salt of fluoric acid to increase the permeability of the user's skin. With the user's skin more permeable, the keratin is able to be more fully absorbed and the curative affect of the keratin is maximized.

While the present discussion relates to keratin, those of ordinary skill in the art readily recognize that the invention is not so limited as other active ingredients are also contemplated. Keratin is the preferred active ingredient.

Products containing this invention's mixture increases the solubility or permeability of the keratin. This increased solubility is accomplished due to the nature of chemicals involved. While fluorides are typically stiff and brittle, they are softened significantly by the fluoric acid which also makes the keratin more soluble.

In many applications, the mixture of keratin with fluoric acid needs to be suspended so that the mixture does not precipitate. Suspension is accomplished by blending the mixture with a carboxyl or a gelatin. Those of ordinary skill in the art readily recognize a variety of other additives which can be used to properly suspend the mixture.

Once the mixture has been formed using a suspension mechanism (i.e. carboxyl), it more easily spread and can be applied to specific areas of the user's body without the keratin/fluoric acid spreading or running. One such application contemplated by this invention is the use of a suspended or gelatized mixture being applied to a user's nails to help harden the finger or toe nails. Another application contemplated is the use of gelatized mixture for the treatment of hair and also as an additive for cosmetics.

In some embodiments of the invention, the suspended or gelatized mixture of keratin/fluoric acid is applied to a paper sheet or other suitable substrate and packaged for single use application. In this manner, the user needs only open the package and spread the keratin/fluoric acid onto the affected area to obtain the desired treatment.

Keratin is any of various albuminoids characteristic of epidermal derivatives, such as nails and feathers, which are insoluble in protein solvents, have a high sulfur content, and generally contain cystine and arginine as the predominating amino acids.

Keratin has been shown to exhibit a wide variety of desirable pharmaceutical properties such as that described in U.S. Pat. No. 4,959,213, issued to Brod et al. on Sep. 25, 1990, and entitled "Pharmaceutical Composition for Treatment and/or prevention of diseases of the skin involving an Inflammatory Process", incorporated hereinto by reference. The Brod patent describes keratin's affect on erythema and acne.

Through the use of a metallic sale of fluoric acid, keratin becomes much more permeable.

Hydrofluoric acid is an aqueous solution of hydrogen fluoride (HF). The material is typically a colorless, fuming, poisonous liquid and is extremely corrosive. It is a weak acid compared to hydrochloric acid but will attack glass and other silica materials. It is often used to polish, frost, or etch glass and to pickle copper, brass, and alloy steels, to clean stone and brick and to acidize oil wells, and also to dissolve ores.

A salt is the reaction product when a metal displaces the hydrogen of an acid. As example, sodium fluoride (NaF) is formed by adding sodium carbonate to hydrofluoric acid.

The metallic salt of hydrofluoric acid, when combined with keratin, significantly increases the passage of the keratin through the skin so that the keratin has significantly more affect.

The action of the salt of hydrofluoric acid is increased through the use of either water or alcohol. The water or alcohol provides a solvent to assist in the through mixing of the salt of hydrofluoric acid with the keratin.

The composition so formed is useful for pharmaceutical treatments, topical cleansers, soaps, creams, and as additives to a variety of cosmetics.

In the preferred embodiment, by weight, the metallic salt of hydrofluoric acid constitutes less than twenty percent of the keratin/hydrofluoric acid salt combination. The actual relative amounts are chosen to obtain the desired results for the contemplated application. Such applications include topical cosmetics, creams, soaps, and additives for pharmaceuticals.

As those of ordinary skill in the art recognize, a soap is a type of detergent in which the water-solubilizing group is a carboxylate, COO—, and the positive ion is usually sodium or potassium.

In the case of some creams, the cream, containing both keratin and the salt of hydrofluoric acid, is applied to the user's epidermal and then left to have it curative affect.

The invention, using a salt of hydrofluoric acid within a topically applied medium, significantly increases the permeability of the user's skin so that the active ingredient is more effective.

In another use of the present invention, the fluoric acid is used as an additive in the laundry to assist in the removal of dirt, grime, and stains. In experimentation, it has also been found that the fluroic acid, when used in a wash of detergent, tends to "fluff" or rejuvenate the pile of the garment.

A theory as to why the fluoric acid has such an affect in the cleaning of garments is based upon the above description concerning the affect that fluoric acid has upon keratin. All clothing has an amount of keratin within its fibers due to the natural sloughing of skin of a human. This keratin "bonds" with the fibers of the garment and make the cleaning of the garment more difficult. Fluoric acid though "softens" the keratin allowing it to be more easily washed from the garment.

A variety of mechanisms to apply the fluroic acid to the wash are contemplated by this invention and include: having the fluroic acid tried onto a cloth-like fiber which is added to the wash; mixing dried fluroic acid to traditional detergent; and adding a diluted liquid form of the fluroic acid. Those of ordinary skill in the art readily recognize a variety of other mechanisms which can be employed in this context.

The quantity of fluroic acid which is used in this context is extremely small. Some experiments have found that two grams of fluoric acid is sufficient for a standard load of clothes. The preferred range of fluoric acid used within a standard load is in the range of 0.5 grams to 500 grams while a typical upper limit is 100 grams.

The invention, together with various embodiments thereof, will be more fully explained by the accompanying drawings and the following description.

DRAWINGS IN BRIEF

FIGS. 1A and 1B illustrate the steps taken in the production of the mixture for two embodiments of the invention.

FIG. 2 illustrates an embodiment of the invention used for the treatment of nails as used in a soak arrangement.

FIGS. 5A and 5B illustrate the use of the invention in liquid form for a traditional washing machine.

FIG. 6 illustrates the preferred embodiment of the invention in which the fluoric acid has been impregnated into disposable absorbent sheets.

FIG. 7 illustrates an alternative embodiment of the invention in which a single application of detergent and fluoric acid have been placed together, an capsule in this illustration.

DRAWINGS IN DETAIL

Figure 3:
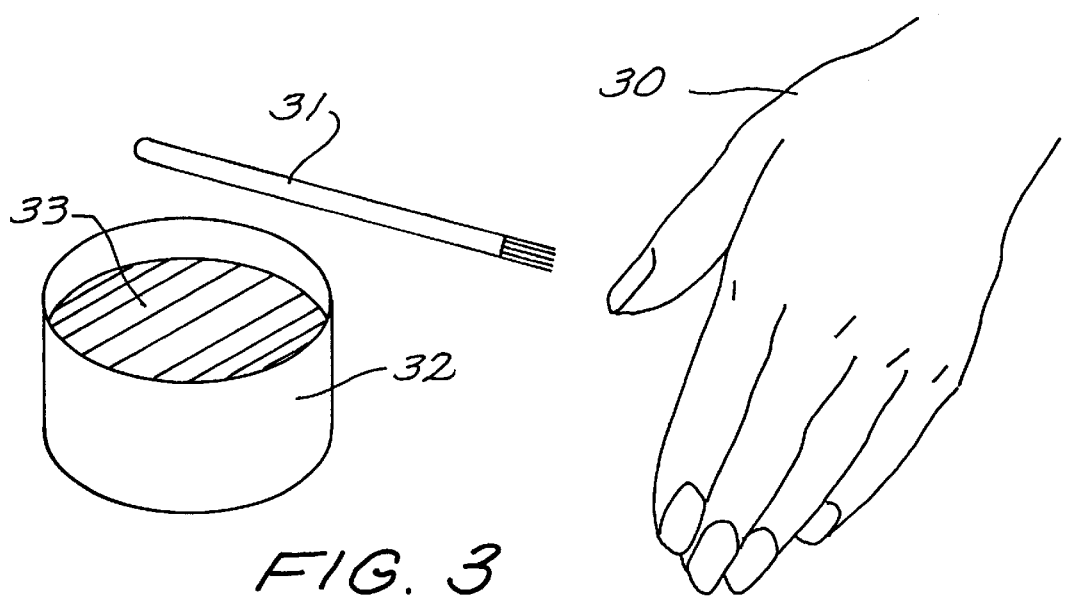
FIG. 3 illustrates an embodiment of the invention which is applied to the nails using a brush.

FIGS. 1A and 1B illustrate the steps taken in the production of the mixture for two embodiments of the invention.

Referring to FIG. 1A, into container 10A is placed the keratin 11, the salt of hydrofluoric acid 12, and a quantity of water 13. This mixture is the suspended through the use of a thickening agent 14 (i.e. carboxyl or a gelatin). Container 10B is then mixed 16 to form a uniform blending of the mixture.

The combination so formed, in container 10C, is then packaged 17 in small bottles for distribution to consumers.

The mixture is distributed in a different manner for the production process shown in FIG. 1B. The mixture from container 10C is applied to substrate 8 using roller 7 as substrate 8 is pulled from source roller 9.

The substrate/mixture combination is then cut by blades 6A and 6B and packaged in single use packages 5.

FIG. 2 illustrates an embodiment of the invention used for the treatment of nails as used in a soak arrangement.

As illustrated, user 20 places a finger in dispenser 21 which contains a mixture 22 of keratin and salt of fluoric acid. The soaking arrangement, due to the enhanced solubility of the keratin caused by the salt of fluoric acid, readily penetrates the finger nails of user 20 so that the nails are properly treated by the keratin.

FIG. 3 illustrates an embodiment of the invention which is applied to the nails using a brush.

As discussed relative to FIG. 2, the combination of keratin and salt of fluoric acid is highly permeable and is beneficial for the treatment of nails and hair. In FIG. 3, application of the keratin/fluoric acid combination 33, is accomplished by using brush 31 to apply the mixture from container 32 onto the nails of user 30.

In another embodiment of the invention, the keratin/fluoric acid mixture is combined with a soap allowing the mixture to be applied directly onto the user's hair for the strengthening of the hair.

Figure 4:
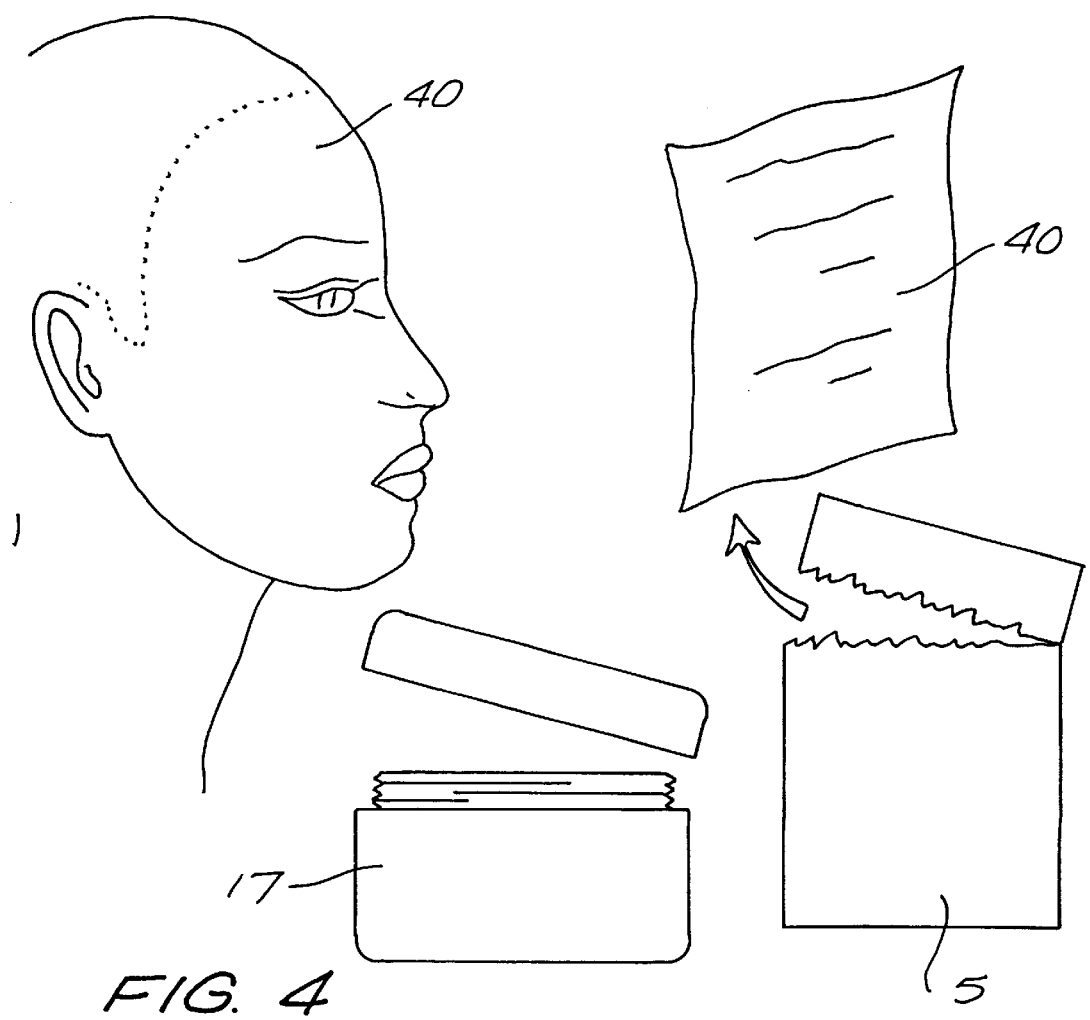
FIG. 4 illustrates two embodiments of the invention being used as a cosmetic.

FIG. 4 illustrates two embodiments of the invention being used as a cosmetic.

In this illustration, user 40 is able to apply the cosmetic from bottle 17 directly onto her face. This external topical application of the mixture of keratin/salt of fluoric acid has great therapeutic affects as the keratin has been rendered highly soluble due to the salt of fluoric acid.

As an alternative, user 40 is able to open package 5 and withdraw a single use sheet 40 which has the mixture of keratin/salt of fluoric acid thereon.

FIGS. 5A and 5B illustrate the use of the invention in liquid form for a traditional washing machine.

As shown in FIG. 5A, at or before the wash cycle of washing machine 50, detergent 51 and fluoric acid are added. The machine mixes water with these two to cleans the soiled garments within its tub. As is usual, once the wash cycle has been completed, the water within the tub is drained and the garments are rinsed with clean water.

FIG. 5B shows how the proper concentration of fluoric acid is obtained for application as outlined in FIG. 5A. Into bottle 55 is deposited a pre-determined amount of fluoric acid 54. Using water 53, the fluoric acid 54 is diluted so that the proper concentration is achieved. In this manner, as example, the operator knows that eight ounces of dilute is to be added to a standard wash to obtain the application of the sought after amount of fluoric acid (ideally between 0.5 grams and 500 grams).

FIG. 6 illustrates the preferred embodiment of the invention in which the fluoric acid has been impregnated into disposable absorbent sheets.

As shown in this illustration, absorbent sheets 61A and 61B are contained within box 60. When the operator desires to apply the specified amount of fluoric acid, sheet 61B is withdrawn and placed within the washing machine as discussed relative to FIG. 5A. Sheets 61A and 61B are made of absorbent material such a linen and each have been impregnated with the specified amount of fluoric acid.

In this way, the operator is assured of placing the proper amount within the wash without having to measure. Once used, the spent sheet is discarded.

FIG. 7 illustrates an alternative embodiment of the invention in which a single application of detergent and fluoric acid have been placed together, an capsule in this illustration.

In this illustration, the detergent and fluoric acid have been mixed with each other and have been encapsulated into a capsule 70. A single capsule contains the proper amount of detergent and also the proper amount of fluoric acid for a single wash and is completely dissolved during the wash cycle.

It is clear from the foregoing that the present invention creates a highly improved apparatus and method of cleaning.

What is claimed is:

1. A method of washing comprising the steps of:
    a) while washing a soiled garment in water, releasing a quantity of fluoric acid into said water; and,
    b) flushing said garment with fresh water.

2. The method of washing according to claim 1, further including the step of, while washing said soiled garment, depositing a preselected quantity of detergent into said water.

3. The method of washing according to claim 2, wherein the step of releasing a quantity of fluoric acid includes the step of assuring that the quantity of fluoric acid is at least half of one gram and less than 500 grams.

4. The method of washing according to claim 3, further including the step of depositing, into said water, an absorbent material having the quantity of fluoric acid impregnated therein.

5. The method of washing according to claim 3, further including the steps of:
    a) diluting said fluoric acid; and,
    b) depositing a selected volume of dilute into said water.

6. The method of washing according to claim 5, wherein the step of diluting said fluoric acid includes the steps of:
    a) depositing a preselected amount of fluoric acid into a container; and,
    b) adding a preselected amount of water to said container.

7. The method of washing according to claim 1, further including the steps of:
    a) creating a mixture of fluoric acid and detergent; and,
    b) placing a selected amount of said mixture into said water.

8. The method of washing according to claim 7, further including the step of encapsulating said mixture of fluoric acid and detergent into said selected amount of said mixture.

9. A method of washing comprising the steps of:
    a) while washing an article in water, depositing,
        1) a preselected quantity of detergent, and,
        2) a selected quantity of fluoric acid into said water;
    b) agitating said water; and,
    c) flushing said article with fresh water.

10. The method of washing according to claim 9, further including the step of assuring that the quantity of fluoric acid in said water is at least one-half of one gram.

11. The method of washing according to claim 9, wherein the step of depositing a quantity of fluoric acid includes the step of: mixing with said article in said water, an absorbent material having the quantity of fluoric acid impregnated therein.

12. The method of washing according to claim 9, further including the step of, creating a mixture of fluoric acid and detergent prior to the step of depositing.

* * * * *